United States Patent [19]
Lieberman

[11] Patent Number: 5,707,631
[45] Date of Patent: Jan. 13, 1998

[54] THERAPEUTIC HERBAL COMPOSITION

[75] Inventor: Chaim J. Lieberman, Monsey, N.Y.

[73] Assignee: Advanced Plant Pharmaceuticals Incorporated, Monsey, N.Y.

[21] Appl. No.: 641,368

[22] Filed: Apr. 30, 1996

[51] Int. Cl.⁶ .................................................. A61K 35/78
[52] U.S. Cl. ..................... 424/195.1; 514/824; 514/825
[58] Field of Search ................... 424/195.1; 514/824, 514/825

[56] References Cited

FOREIGN PATENT DOCUMENTS

WO94 18994  9/1994  WIPO .

*Primary Examiner*—John W. Rollins
*Attorney, Agent, or Firm*—Coleman & Sudol

[57] ABSTRACT

A therapeutic herbal composition including *Trigonella foenum-graecum* seed, *Syzygium aromaticum* fruit, *Allilum sativum* bulb, *Cinnamonmum zyelanicum* bark, *Saussurea costus* root and *Euphorbia lathyris* bud which includes an effective amount of sodium chloride to promote the digestibility and storage stability of the compositions, have been shown effective in reducing cholesterol, and triglycerides. This herbal composition has use in lowering cholesterol and treating arthritis, blood pressure and Alzheimer's disease. It is also effective as a bitters tonic.

15 Claims, No Drawings

THERAPEUTIC HERBAL COMPOSITION

BACKGROUND OF THE INVENTION

The subject invention relates generally to a therapeutic herbal composition, and in particular to a herbal composition which includes *Trigonella foenum-graecum* seed, *Syzygium aromaticum* fruit, *Allilum sativum* bulb, *Cinnamonmum zyelanicum* bark, *Saussurea costus* root and *Euphorbia lathyris* bud. This therapeutic herbal composition is formed from a synergistic combination of herbs which are useful in lowering cholesterol, and treating arthritis, blood pressure and Alzheimer's disease. It is also useful as a bitters tonic, and has been approved as a bitters tonic by the Australian Therapeutic Goods Administration.

Although the use of various herbs have been described in related areas, the synergistic combination of the subject invention has never previously been described.

Japanese Patent Publication No. 4,005,237 teaches the combination of *Cinnamomum sieboldii* and *Allium sativum* for superoxide scavenging in the treatment of inflammatory disorders. German Patent Publication No. 3,724,341 teaches the use of *Cinnamomum zeylanicum* as an anti-inflammatory agent which exerts a synergistic anti-inflammatory effect in combination with *Pumica granitum* cortex, *Cardamon zingiberaceie* fruit and *Piper longum* fruit.

PCT Application PCT/US94/02184, published as WO 94/18994, is directed to a therapeutic herbal composition formed from the disclosed herbs. This reference does not disclose the unexpected activity related to the digestibility of the compounds as well as the storage stability which characterizes compositions to which effective concentrations of sodium chloride, more preferably, sea salt, have been added.

In view of the above, there exists a great need for therapeutic compositions useful in lowering cholesterol, and treating arthritis, blood pressure and Alzheimer's disease. Although not wishing to be bound by theory, it is believed that the composition of herbs described herein in combination with the effective amounts of sea salt, functions to produce a synergistic interaction combined with favorable digestibility and storage stability characteristics, and thus represents a viable treatment of high cholesterol, arthritis, high blood pressure and Alzheimer's disease, as well as a general bitters tonic.

SUMMARY OF THE INVENTION

The subject invention provides a therapeutic composition which comprises *Trigonella foenum-graecum* seed, *Syzygium aromaticum* fruit, *Allilum sativum* bulb, *Cinnamonmum zyelanicum* bark, *Saussurea costus* root, and *Euphorbia lathyris* bud in amounts effective to produce a physiological benefit in combination with an amount of sodium chloride, more preferably sea salt, which is effective to promote the digestibility (palatability) and storage stability of the therapeutic composition.

DETAILED DESCRIPTION OF THE INVENTION

The term "patient" or "subject" is used throughout the specification to describe a human to whom treatment with the compositions and methods according to the present invention is provided.

The term "effective concentration" or "effective amount" is used to describe an mount or concentration of an active agent or composition according to the present invention which is used in the present invention to produce an intended result. In the case of the present invention, effective concentrations are generally concentrations which are effective in reducing cholesterol, treating arthritis, blood pressure and Alzheimer's disease, which may include concentrations of the active agent which prevent these conditions as well. The term effective concentration or amount subsumes the administraton of a pharmaceutically active agent according to the present invention for a period consistent with the realization of the intended result. Effective amounts of the compounds which are used according to the present invention include amounts which comprise approximately 250 mg to about 750 mg., more preferably about 600 mg. taken 1 to 8 times per day. These amounts of herbal product produce an effective concentration range in human body fluids, i.e., blood, plasma and serum.

The term "sea salt" is used to describe preferred salt which is used in the present invention to promote the digestibility and storage stability of compositions according to the present invention. Although any source of sodium chloride may be used in the present invention, provided that the amount of sodium chloride represents approximately 1% to about 20% by weight, more preferably about 3% to about 5% by weight of the final composition, salt obtained by the evaporation of salt water obtained from the ocean or sea, and in particular the Dead Sea, is preferred. Although numerous sources of salt are proposed for use in the present invention, one supplier of the preferred Dead Sea Salt is Modin BAM, Israel.

The subject invention will now be described in terms of its preferred embodiments. These embodiments are set forth to aid in the understanding of the subject invention, but are not to be construed as limiting.

The subject composition is that described below:

|  | wt. | % of wt. | % wt. range |
|---|---|---|---|
| *Trigonella foenum-graecum* seed | 305 mg | 52.5 | 5–95 |
| *Syzygium aromaticum* fruit | 55 mg | 9.5 | 1–50 |
| *Allilum sativum* bulb | 55 mg | 9.5 | 1–50 |
| *Cinnamonnum zyelanicum* bark | 55 mg | 9.5 | 1–50 |
| *Saussurea costus* root | 55 mg | 9.5 | 1–50 |
| *Euphorbia lathyris* bud | 55 mg | 9.5 | 1–50 |
|  | 580 mg |  |  |

The composition supplies the physiologically important chemicals listed below:

| | |
|---|---|
| Choline | Calcium |
| Phosphorous | Iron |
| Magnesium | Sodium |
| Potassium | Zinc |
| Vitamin A | Thiamine HCl |
| Riboflavin | Nicotinic Acid |
| Ascorbic Acid | Lecithin |
| Phytosterols | Tryptophane |
| Beta Carotene | Colchicine |

The biological active components include choline and inositol.

The above herbs are typically dried and ground to a fine powder. All weights are expressed in milligrams and all percentages are by weight of the essential elements in the composition. The composition is typically an intimate mixture of powders. However, extracted herbs may also be used. The composition as described above is thereafter combined with an mount of sodium chloride, in amounts effective to render the product more palatable and storage stable. Sea salt is a particularly preferred component containing sodium chloride which may be advantageously added to the present compositions. Sea salt obtained from the Dead Sea is particularly preferred. It is an unexpected result that the inclusion of sodium chloride in amounts ranging from about 1.0% to about 20%, more preferably about 3% to about 5% by weight of the composition comprising the above-described six herbal components will produce a particularly effective and palatable composition exhibiting good digestibility and storage stability (i.e., for periods of at least one month, more preferably at least about six months, and even 1 year or longer). While not being limited by way of theory, it is believed that the inclusion of salt within the above-described weight ranges maintains and/or enhances the activity of the composition and instills favorable characteristics of digestibility and storage stability to the compositions by decreasing the hygroscopic character of the herbal mixture in the absence of the salt.

The known biological active components include choline and thiamine. Under normal conditions a 580 mg dose of the herbal components would be administered several times daily. However, under general conditions, in order to unexpectedly increase the digestibility and the storage stability of the herbal composition, the dosage is combined with from about 1% to about 20% by weight of sodium chloride, preferably as sea salt. The dosage of course may vary depending on body weight and other conditions readily determinable by those skilled in the art who have read the subject application.

Administration is typically oral, with administration being via a capsule. In addition to the above herbs, various pharmaceutically acceptable addtives, excipients and fillers, such as ash, may be present.

The following study was done to evaluate the efficacy of the subject composition. Four hundred people, in groups of one hundred people each, took part in the study as follows:

100 people on a weight loss and lower lipid diet and taking the subject composition.
   100 people on a weight loss and lower lipid diet and taking a placebo.
   100 people without the diet and taking the subject composition.
   100 people without diet and taking a placebo.

All subjects were referred to by general practitioners, and details of medical status, including previous illnesses, medication and blood pressure, were kept.

The following evaluations were performed:
   Check on weight
   Interview with dietician monitoring daily dietary intake
   Checks on lipids and liver enzymes
   Determination of likelihood of compliance The purpose of the study was to determine whether the subject composition taken in capsule form 680 mg each (580 mg of the composition) and including approximately 3% by weight sea salt, obtained as Dead Sea Salt from Modin BAM, Israel, twice daily for 18 weeks, lowers:
   Total Cholesterol
   Triglycerides
   APO A1 B2
   RATIO
   Increase HDL From the above trial, 200 subjects receiving a placebo (a combination of soya bean flower and sugar) showed no significant changes at the end of 10 weeks and treatment was discontinued.

From the 100 subjects treated with diet and the subject composition, eight discontinued treatment after six weeks, fifteen discontinued after fifteen weeks and one died. Based on fifteen weeks of treatment with diet, it was noted that there was a decrease in cholesterol and triglycerides by an average of 22%.

Of the 100 subjects taking the subject composition together with diet, 76 subjects reported constitutional weight loss averaging 9 kg.
   Total cholesterol decrease by 58%
   Triglyceride decreased by 61%
   LDL/VLDL decrease by 29%
   Ratio decrease by up to 75%
   HDL increase by average of 80%

Of the 100 subjects taking the subject composition without diet, six subjects discontinued treatment due to strong body odor and balance of 94 subjects reported constitutionally:

51 subjects- Cholesterol reduced by 8–15%
                Triglyceride reduced by 30–42%
                LDL/VLDL reduced by 6–19%
                Ratio Reduced by 14–33%
                HDL increased by 62%
   43 subjects- Cholesterol reduced by 3–11%
                Triglyceride reduced by 15–30%
                LDL/VLDL reduced by 1–7%
                Ratio Reduced by 9–20%
                HDL increased by 22%
   Dosage for study: 12 capsules per day for the first 6 weeks.
                Thereafter reduced to 8 capsules per day
                (equivalent to 1 capsule per 6.7 kg of body weight).

Empirical evidence from laboratory tests attests to the good efficacy of capsules containing the subject composition during its two years shelf life, due primarily to the inclusion of effective amounts of sea salt. The main bioactive ingredients include choline, thiamine HCl, ascorbic acid, nicotinic acid, lecithin and phytosterols, which are reported by the British Pharmacopoeia to be effective against coronary atherosclerosis and lowering high cholesterol and triglyceride levels. The hygroscopicity to moisture content varies during storage and distribution from 6.8% to 10% while maintaining normal function. In the case of the inclusion of effective amounts of sodium chloride, the hydroscopicity is markedly reduced.

The biodecomposition in digestibility test within 0.2% pepsin solution complies with analysis of Association of Analytical Chemists for 28% digestive residue at temperature 42°45° C. during 16 hours supporting good quality herbal ingredients. Clinical research shows that ratios of HDL (High Density Lipoproteins) to LDL (Low Density Lipoproteins) lies in their respective functions for reduced blood cholesterol levels.

Normally the powder is encapsulated in moisture permeable gelatin doses of zero size and next is stored in 350 mls polyvinyl chloride bottles at range temperature 20°–30° C. This prevents powder texture, white color and a bioactivity from changing as a result of variations in night and day temperatures, as well as keeping smell and taste unchanged during storage. Moreover, the cholesterol lowering action of the subject composition is stabilized by radiation sterilization or using ethylene oxide penetration at elevated temperature, i.e. about 70° C.

The stability data do not contain detectable concentration of degradation substances and periodical bacteriological tests under a high humidity environment proved satisfactory.

Upon reading the subject application, various embodiments will become obvious to those skilled in the art. These embodiments are to be considered within the scope and spirit of the subject invention which is only to be limited by the claims which follow and their equivalents.

What is claimed is:

1. An oral therapeutic composition which comprises *Trigonella foenum-graecum* seed, *Syzygium aromaticum* fruit, *Allilum sativum* bulb, *Cinnamonmum zyelanicum* bark, *Saussurea costus* root, and *Euphorbia lathyris* bud in amounts effective to produce a physiological benefit in combination with an amount of sodium chloride effective to substantially promote the digestibility and storage stability of the composition.

2. The composition according to claim 1, wherein the *Trigonella foenum-graecum* seed is present in an amount of from about 5 to about 95 weight percent of the composition, *Syzygium aromaticum* fruit is present in an amount of from about 1 to about 50 weight percent of the composition, *Allilum sativum* bulb is present in an amount from about 1 to about 50 weight percent of the composition, *Cinnamonmum zyelanicum* bark is present in an amount from about 1 to about 50 weight percent of the composition, *Saussurea costus* root is present in an amount from about 1 to about 50 weight percent of the composition, and *Euphorbia lathyris* bud is present in an amount from about 1 to about 50 weight percent of the composition.

3. The composition according to claim 2, wherein the *Trigonella foenum-graecum* seed is present in an amount of about 52.0% by weight of the composition, *Syzygium aromaticum* fruit is present in an amount of about 9.0% by weight of the composition, *Allilum sativum* bulb is present in an amount of about 9.0% by weight of the composition, *Cinnamonmum zyelanicum* bark is present in an amount of about 9.0% by weight of the composition, *Saussurea costus* root is present in an amount of about 9.0% by weight of the composition, and *Euphorbia lathyris* bud is present in an amount of about 9.0% by weight of the composition, the composition further including sea salt in an amount of about 3% by weight of the composition.

4. The composition according to claim 1 further comprising a pharmaceutically acceptable additive, excipient or filler.

5. The composition according to claim 4 wherein said additive is ash.

6. A capsule comprising the composition of claim 1.

7. The capsule according to claim 6, wherein the *Trigonella foenum-graecum* seed is present in an amount of about 52.0% by weight of the composition, *Syzygium aromaticum* fruit is present in an amount of about 9.0% by weight of the composition, *Allilum sativum* bulb is present in an amount of about 9.0% by weight of the composition, *Cinnamonmum zyelanicum* bark is present in an amount of about 9.0% by weight of the composition, *Saussurea costus* root is present in an amount of about 9.0% by weight of the composition, and *Euphorbia lathyris* bud is present in an amount of about 9.0% by weight of the composition, the composition further including sodium chloride in an amount of about 3% by weight of the composition.

8. The capsule according to claim 6, wherein the *Trigonella foenum-graecum* seed is present in an amount of about 305 mg, *Syzygium aromaticum* fruit is present in an amount of about 55 mg, *Allilum sativum* bulb is present in an amount of about 55 mg, *Cinnamonmum zyelanicum* bark is present in an amount of about 55 mg, *Saussurea costus* root is present in an amount of about 55 mg, and *Euphorbia lathyris* bud is present in an amount of about 55 mg, said composition further comprising about 1% to about 20% by weight of sea salt.

9. An oral therapeutic composition which comprises *Trigonella foenum-graecum* seed, *Syzygium aromaticum* fruit, *Allilum sativum* bulb, *Cinnamonmum zyelanicum* bark, *Saussurea costus* root, and *Euphorbia lathyris* bud in amounts effective to produce a physiological benefit in combination with about 1% to about 20% by weight of sodium chloride.

10. The composition according to claim 9, wherein the *Trigonella foenum-graecum* seed is present in an amount of from about 5 to about 95 weight percent of the composition, *Syzygium aromaticum* fruit is present in an amount of from about 1 to about 50 weight percent of the composition, *Allilum sativum* bulb is present in an amount from about 1 to about 50 weight percent of the composition, *Cinnamonmum zyelanicum* bark is present in an amount from about 1 to about 50 weight percent of the composition, *Saussurea costus* root is present in an amount from about 1 to about 50 weight percent of the composition, and *Euphorbia lathyris* bud is present in an amount from about 1 to about 50 weight percent of the composition and said sodium chloride is included as sea salt.

11. The composition according to claim 10, wherein the *Trigonella foenum-graecum* seed is present in an amount of about 52.0% by weight of the composition, *Syzygium aromaticum* fruit is present in an amount of about 9.0% by weight of the composition, *Allilum sativum* bulb is present in an amount of about 9.0% by weight of the composition, *Cinnamonmum zyelanicum* bark is present in an amount of about 9.0% by weight of the composition, *Saussurea costus* root is present in an amount of about 9.0% by weight of the composition, and *Euphorbia lathyris* bud is present in an amount of about 9.0% by weight of the composition, said sea salt being included in an amount of about 3% to about 5% by weight of said composition.

12. The composition according to claim 9 further comprising a pharmaceutically acceptable additive, excipient or filler.

13. The composition according to claim 12 wherein said additive is ash.

14. A capsule comprising the composition of claim 9.

15. The capsule according to claim 9, wherein the *Trigonella foenum-graecum* seed is present in an amount of about 52.0% by weight of the composition, *Syzygium aromaticum* fruit is present in an amount of about 9.0% by weight of the composition, *Allilum sativum* bulb is present in an amount of about 9.0% by weight of the composition, *Cinnamonmum zyelanicum* bark is present in an amount of about 9.0% by weight of the composition, *Saussurea costus* root is present in an amount of about 9.0% by weight of the composition, and *Euphorbia lathyris* bud is present in an amount of about 9.0% by weight of the composition, said sodium chloride being included an amount of about 3% by weight of said composition.

* * * * *